US006613713B2

(12) United States Patent
Becke et al.

(10) Patent No.: US 6,613,713 B2
(45) Date of Patent: *Sep. 2, 2003

(54) ORGANOMETALLIC COMPOUNDS WITH FUSED INDENYL LIGANDS

(75) Inventors: Sigurd Becke, Rösrath (DE); Heinrich Lang, Chemnitz (DE); Thomas Weiss, Mannheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 186 days.

This patent is subject to a terminal disclaimer.

(21) Appl. No.: 09/767,491

(22) Filed: Jan. 23, 2001

(65) Prior Publication Data

US 2001/0014725 A1 Aug. 16, 2001

(30) Foreign Application Priority Data

Jan. 28, 2000 (DE) .......................... 100 03 581

(51) Int. Cl.$^7$ .............. B01J 31/38; C08F 4/72; C07F 17/00
(52) U.S. Cl. ............ 502/104; 502/152; 502/155; 556/11; 556/12; 556/20; 556/43; 556/53; 556/54; 526/127; 526/160; 526/161; 526/943
(58) Field of Search ................ 556/11, 12, 13, 556/20, 43, 53; 586/54; 526/127, 128, 160, 943; 502/117, 152

(56) References Cited

U.S. PATENT DOCUMENTS

| 5,026,798 A | 6/1991 | Canich ................ 526/127 |
| 5,145,819 A | 9/1992 | Winter et al. ............ 502/117 |
| 5,276,208 A | 1/1994 | Winter et al. ............ 556/53 |
| 6,015,868 A | 1/2000 | Nickias et al. .......... 526/127 |
| RE37,208 E * | 6/2001 | Winter et al. ............ 526/348 |
| 6,248,912 B1 * | 6/2001 | Lang et al. .............. 556/11 |
| RE37,384 E * | 9/2001 | Winter et al. ............ 502/117 |

FOREIGN PATENT DOCUMENTS

| EP | 277003 | 8/1988 |
| EP | 277004 | 8/1988 |
| EP | 941997 | 9/1999 |
| WO | 94/11406 | 5/1994 |
| WO | 98/09999 | 3/1998 |
| WO | 98/27103 | 6/1998 |
| WO | 98/49212 | 11/1998 |

OTHER PUBLICATIONS

Foster, Patrick et al: "Synthesis and polymerization behavior of tetrahydro–2–methylbenzindenyltitanium and zirconium compounds" Journal of Organomettallic Chemistry (1998), 571(2), 171–181 XP004142026 das ganze dokument.

Organometallies, 13, (month unavailable) 1994, pp. 964–970, U. Stehling et al, "ansa–Zirconocene Polymerization Catalysts with Annelated Ring Ligands—Effects on Catalytic Activity and Polymer Chain Length[1]".

Organometalies, 12, (month unavailable) 1993, pp. 5012–5015, M. H. Nantz et al, "A Disulfone–Based Approach to ansa–Titanocenes: Synthesis of (Ethylenebis(2–indenyl))titanium Dichloride".

Journal of Organometallic Chemistry, 568 (month unavailable) 1998, pp. 41–51, R. L. Halterman et al, "Synthesis and structure of [1,2–bis(1–indenyl)benzene]titanium and zirconium dichlorides".

Organometallics, 16, (month unavailable) 1997, pp. 842–857, L. Jia et al, "Cationic Metallocene Polymerization Catalysts Based on Tetrakis(pentafluorophenyl)borate and Its Derivatives. Probing the Limits of Anion "Noncoordination" via a Synthetic, Solution Dynamic, Structural, and Catalytic Olefin Polymerization Study" and Supplementary Material, pp. 1–50.

\* cited by examiner

Primary Examiner—Robert D. Harlan
(74) Attorney, Agent, or Firm—Joseph C. Gil; Jennifer R. Seng; Noland J. Cheung

(57) ABSTRACT

The present invention relates to transition metal organometallic compounds with an indenyl ligand attached in position 2 and fused in position 5,6, to a process for the production thereof and to the use thereof as catalysts for the (co)polymerization of olefinic and/or diolefinic monomers.

12 Claims, No Drawings

ORGANOMETALLIC COMPOUNDS WITH FUSED INDENYL LIGANDS

FIELD OF THE INVENTION

The present invention relates to transition metal organometallic compounds with an indenyl ligand attached in position 2 and fused in position 5,6, and also to a process for the production thereof and to the use thereof as catalysts for the (co)polymerization of olefinic and/or diolefinic monomers.

BACKGROUND OF THE INVENTION

In accordance with IUPAC nomenclature, the positions of the ring atoms of indene are designated as follows in the present application:

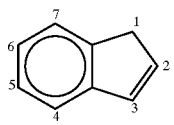

Stereo-rigid chiral metallocenes having bridged indenyl ligands are known as catalysts for the production of polyolefins. It has been found in this connection that the nature and position of the substituents on the indenyl anion and the nature and position of the bridging have an influence both upon catalyst activity and upon polymer properties. Many indenyl metallocenes are bridged in position 1 (1-indenyl metallocenes).

Bis(1-indenyl) metallocenes substituted in position 2 and/or 4 with indenyl residues bridged in position 1 are of particular significance in the production of highly isotactic polypropylene having elevated crystallinity and an elevated melting point. (EP-A1-485 821, EP-A1-485 823, EP-A2-519 237). Bis(1-indenyl) metallocenes benzo-fused in position 4,5 are also of significance (c.f. *Organometallics* 1994, 13, 964–970).

It is also known to use organometallic compounds with only one indenyl anion as catalysts (constrained geometry complexes with 1-indenyl ligands, c.f. U.S. Pat. No. 5,026,798, WO-97/15583-A1).

WO-94/11406-A1 discloses transition metal organometallic compounds which comprise one indenyl and one cyclopentadienyl ligand, wherein the indenyl ligand is substituted in position 2; this substituent may also act as a bridge to the second ligand. The practical Examples show multistage production processes with highly unsatisfactory yields which, in the case of bridged compounds, give rise to 1-cyclopentadienyl-2-(2-indenyl)ethanezirconium chloride, to bis(2-indenyl)methanezirconium chloride or to dimethyl-bis(2-indenyl)silanezirconium dichloride, which still contains impurities. *Organometallics* 1993, 12, 5012–5015 describes a multistage synthesis pathway to ethylenebis(2-indenyl)titanium dichloride. Due to the multistage synthesis and the numerous purification operations, the achievable yield is very low. Due to the synthesis pathway, the structural variety of ethylene-bridged ligands is limited.

EP-A-2-941 997 discloses ethylene-bridged bis(2-indenyl)zircono-cenes. These zirconocenes are used for the production of special low molecular weight polyolefins.

EP-A1-940 408 describes silyl-bridged 2-indenyl metallocenes and a process for the production of organometallic compounds with indenyl ligands attached in position 2.

Comparatively little is known about organometallic compounds with indenyl ligands fused in position 5,6 (for example tetrahydroindacenyl ligands). Example 3 of WO-98/09999-A1 discloses the production of a half-sandwich titanium complex with a tetrahydroindacenyl ligand. Availability of the tetrahydroindacenyl titanium complex bridged in position 1 is, however, unsatisfactory (overall yield <1%). WO-98/49212-A1 and WO-98/27103-A1 describe the production of half-sandwich complexes with tetrahydroindacenyl ligands bridged in position 1 and substituted in position 2 and/or 3 and the use thereof as catalysts for polymerizing olefins.

Transition metal complexes with tetrahydroindacenyl ligands bridged in position 2 are not known.

SUMMARY OF THE INVENTION

It has now been found that such organometallic catalysts, the bridging of which begins in position 2 of at least one tetrahydroindacenyl anion, have particular characteristics as polymerization catalysts, in particular producing largely atactic polymers having elevated molecular weights in the (co)polymerization of α-olefins. It was accordingly desirable to find a production process for such catalysts bridged in position 2 of at least one tetrahydroindacenyl anion.

Another object was to provide a catalyst which is suitable for synthesizing high molecular weight EPDM.

DETAILED DESCRIPTION OF THE INVENTION

The present invention relates to a process for the production of transition metal organometallic compounds with 2-indenyl fused in position 5,6 as the first ligand of the formula

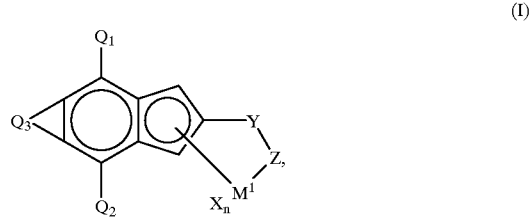

(I)

in which $Q^1$, $Q^2$ are identical or different and, as a substituent of the 2-indenyl system fused in position 5,6, mean hydrogen, $C_1$–$C_4$ alkyl, $C_6$–$C_{14}$ aryl, $C_7$–$C_{10}$ aralkyl, $C_1$–$C_4$ alkoxy, $C_1$–$C_4$ alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ represents an optionally substituted alkylene residue which, together with the two carbon atoms of the indenyl residue, forms a ring system in position 5 and 6, $M^1$ is a transition metal from groups 4, 5 or 6 of the IUPAC 1985 periodic system of elements, X means an anion, n is a number from zero to four, which is determined by the valency and bond state of $M^1$, Y represents a bridge from the group of —C($R^1R^2$)—, —Si($R^1R^2$)—, —Ge($R^1R^2$)—, —C($R^1R^2$)—C $(R^3R^4)$—, —$C(R^1R^2)$—$Si(R^3R^4)$— or —$Si(R^1R^2)$—$Si(R^3R^4)$—, in which $R^1$, $R^2$, $R^3$ and $R^4$ mutually independently mean hydrogen, halogen, linear or branched $C_1$–$C_{10}$ alkyl, $C_5$–$C_8$ cycloalkyl, $C_6$–$C_{14}$ aryl or $C_7$–$C_{10}$ aralkyl and Z is a second ligand from the group of open-chain and cyclic, optionally anionic π-systems, —$N(R^5)$—, $P(R^6)$—, $|N(R^5R^7)$, $|P(R^6R^8)$—, —O—, —S—, $|OR^5$— or $|SR^5$—, wherein the vertical line to the left of the element symbol N, P, O or S means an electron pair and the bond between Z and $M^1$ is of an ionic, covalent or coordinative nature and in which $R^5$, $R^6$, $R^7$ and $R^8$ mutually independently have the range of meaning of $R^1$ to $R^4$ and $R^5$ and $R^7$ may additionally mean —$Si(R^1R^2R^3)$ and $R^6$ and $R^8$ may additionally mean —$Si(R^1R^2R^3)$, —$OR^1$, —$SR^1$ or —$N(R^1R^2)$, characterized in that a haloindene fused in position 5,6 of the formula

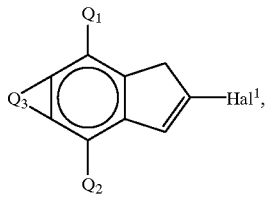

(II)

in which $Hal^1$ denotes Cl, Br or I and $Q^1$, $Q^2$ and $Q^3$ have the above meaning, is reacted with an elemental metal selected from group 1, 2 or 12 of the IUPAC 1985 periodic system or a corresponding metal compound in a quantity in the range from 1 to 100 mol of elemental metal/metal compound per mol of (II) and with a dihalide of the bridge Y of the formula

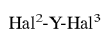

$Hal^2$-Y-$Hal^3$ (III), in which
$Hal^2$ and $Hal^3$ mutually independently mean Cl, Br or I and Y has the above range of meaning, in a quantity of 1 to 20 mol of (III) per mol of (II), wherein in the event that Y has the meaning —$Si(R^1R^2)$—, —$Ge(R^1R^2)$— or —$Si(R^1R^2)$—$Si(R^3R^4)$—, the reaction of (II) with (i) elemental metal/metal compound and (ii) with (III) may also proceed simultaneously, and the reaction product of the formula

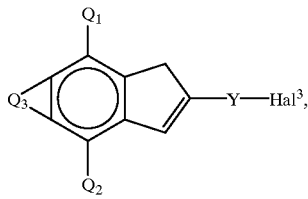

(IV)

in which $Q^1$, $Q^2$, $Q^3$, Y and $Hal^3$ have the above meaning, optionally after the isolation thereof, is reacted with a Z derivative of the formula

$ZM^2_p$ (Va)

or

$ZR^9_p$ (Vb), in which
$M^2$ denotes Li, Na, K or —$MgHal^4$, in which $Hal^4$ has the range of meaning of $Hal^2$, p represents the number one or two,
$R^9$ represents hydrogen, —$Si(R^1R^2R^3)$ or $Sn(R^1R^2R^3)$ and Z, $R^1$, $R^2$ and $R^3$ have the above meaning,
with elimination of a compound of the formula

$M^2Hal^3$ (VIa)

or

$R^9Hal^3$ (VIb)

in which $M^2$, $R^9$ and $Hal^3$ have the above meaning, optionally in the presence of an auxiliary base to yield the 2-indenyl compound of the formula

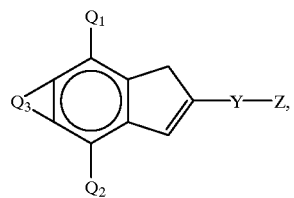

(VII)

in which $Q^1$, $Q^2$, $Q^3$, Y and Z have the above meaning, and which may be present as a dianion and in which Z may furthermore bear $M^2$, $R^9$ or an electron pair, and is then further reacted with a transition metal compound of the formula

$M^1X_q$ (VIII), in which
$M^1$ and X have the above meaning and
q is a number from two to six, which is determined by the oxidation state of $M^1$.

The process is advantageously performed at temperatures in the range from −100 to 120° C.

Metals of groups 1, 2 or 12 which may, in particular, be mentioned are lithium, potassium, sodium, magnesium, calcium, zinc, cadmium and mercury. The metals of groups 2 and 12 are preferred. It may also be advantageous to use the metals as a mixture with each other.

Corresponding metal compounds, which may be mentioned are butyllithium, magnesium-butadiene, magnesium-anthracene and corresponding compounds of the other stated metals.

It may be advantageous to separate the unreacted metals/metal compounds before the addition of (III).

As a rule, the corresponding metal halides metal $Hal^1Hal^2$ are formed on reaction with (III).

Moreover, as a rule, when (Va) or (Vb) are added, the corresponding compounds of the formulae $M^2Hal^3$ (VIa)

or

$R^9Hal^3$ (VIb)

in which
$M^2$, $R^9$ and $Hal^3$ have the stated meanings, are formed.

The invention furthermore relates to the transition metal organometallic compounds with 2-indenyl fused in position 5,6 as the first ligand of the formula which may be produced with the stated process

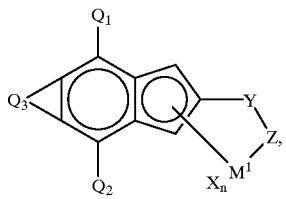

(I)

in which

Q$^1$, Q$^2$ are identical or different and, as a substituent of the 2-indenyl system fused in position 5,6, mean hydrogen, C$_1$–C$_4$ alkyl, C$_6$–C$_{14}$ aryl, C$_7$–C$_{10}$ aralkyl, C$_1$–C$_4$ alkoxy, C$_1$–C$_4$ alkylthio, phenoxy, phenylthio, di-C$_1$–C$_4$-alkylamino, C$_6$–C$_{14}$-aryl-C$_1$–C$_4$-alkylamino, di-C$_6$–C$_{14}$-arylamino, dibenzylamino, tri-C$_1$–C$_4$-alkylsilyl, di-C$_1$–C$_4$-alkylboranyl, phenyl-C$_1$–C$_4$-alkylboranyl, diphenylboranyl, di-C$_1$–C$_4$-alkylphosphoryl, diphenylphosphoryl or phenyl-C$_1$–C$_4$-alkylphosphoryl, Q$^3$ represents an optionally substituted alkylene residue which, together with the two carbon atoms of the indenyl residue, forms a ring system in position 5 and 6, M$^1$ is a transition metal from groups 4, 5 or 6 of the IUPAC 1985 periodic system of elements, X means an anion, n is a number from zero to four, which is determined by the valency and bond state of M$^1$, Y represents a bridge from the group of —C(R$^1$R$^2$)—, —Si(R$^1$R$^2$)—, —Ge(R$^1$R$^2$)—, —C(R$^1$R$^2$)—C(R$^3$R$^4$)—, —C(R$^1$R$^2$)—Si(R$^3$R$^4$)— or —Si(R$^1$R$^2$)—Si(R$^3$R$^4$)—, in which R$^1$, R$^2$, R$^3$ and R$^4$ mutually independently mean hydrogen, halogen, linear or branched C$_1$–C$_{10}$ alkyl, C$_5$–C$_8$ cycloalkyl, C$_6$–C$_{14}$ aryl or C$_7$–C$_{10}$ aralkyl and Z is a second ligand from the group of open-chain and cyclic, optionally anionic π-systems, —N(R$^5$)—, P(R$^6$)—, |N(R$^5$R$^7$)—, |P(R$^6$R$^8$)—, —O—, —S—, |OR$^5$— or |SR$^5$—, wherein the horizontal line to the left of the element symbol N, P, O or S represents a covalent bond between Z and M$^1$, wherein the vertical line to the left of the element symbol N, P, O or S means an electron pair and the bond between Z and M$^1$ is of a coordinative not covalent nature and in which R$^5$, R$^6$, R$^7$ and R$^8$ mutually independently have the range of meaning of R$^1$ to R$^4$ and R$^5$ and R$^7$ may additionally mean —Si(R$^1$R$^2$R$^3$) and R$^6$ and R$^8$ may additionally mean —Si(R$^1$R$^2$R$^3$), —OR$^1$, —SR$^1$ or —N(R$^1$R$^2$).

Compounds of the formula

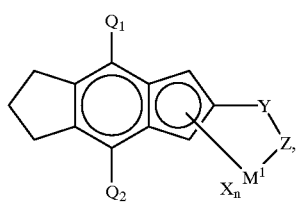

(Ia)

in which Q$^1$, Q$^2$, Y, Z, X, M$^1$ and n have the above meaning are preferred.

The process according to the invention is characterized by a sequence of reactions passing via the intermediate product of the above formula (IV). Such intermediate products have not hitherto been known. The present invention accordingly also relates to these intermediate products.

The invention furthermore relates to a process for the production of the intermediate products of the formula (IV) which is characterized in that a 2-haloindene fused in position 5,6 of the formula

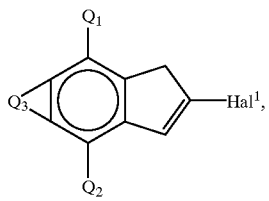

(II)

in which

Hal$^1$, Q$^1$, Q$^2$ and Q$^3$ have the above meaning, is reacted with an elemental metal selected from group 1, 2 or 12 of the IUPAC 1985 periodic system or a corresponding metal compound in a quantity in the range from 1 to 100 mol of elemental metal/metal compound per mol of (II) and with a dihalide of Y of the formula Hal$^2$-Y-Hal$^3$ (III), in which Y, Hal$^2$ and Hal$^3$ have the above meaning, in a quantity of 1 to 20 mol of (III) per mol of (II), wherein in the event that Y has the meaning —Si(R$^1$R$^2$)—, —Ge(R$^1$R$^2$)— or —Si(R$^1$R$^2$)—Si(R$^3$R$^4$)—, the reaction of (II) with (i) elemental metal/metal compound and (ii) with (III) may also proceed simultaneously.

Metals of groups 1, 2 or 12, which may, in particular, be mentioned are lithium, potassium, sodium, magnesium, calcium, zinc, cadmium and mercury. Metals of groups 2 and 12 are preferred. It may also be advantageous to use the metals as a mixture with each other.

Corresponding metal compounds which may be mentioned are butyllithium, magnesium-butadiene, magnesium-anthracene and corresponding compounds of the other stated metals.

It may be advantageous to separate the unreacted metals/metal compounds before the addition of (III).

As a rule, the corresponding metal halides metal Hal$^1$Hal$^2$ are formed on reaction with (III).

Moreover, as a rule, when (Va) or (Vb) are added, the corresponding compounds of the formulae M$^2$Hal$^3$ (VIa)

or

R$^9$Hal$^3$ (VIb)

in which

M$^2$, R$^9$ and Hal$^3$ have the known meanings, are formed.

The process is advantageously performed at temperatures in the range from –100° C. to +120° C.

The invention furthermore relates to a process for the production of the intermediate products of the formula (II), which is characterized in that the optionally substituted indanone of the formula

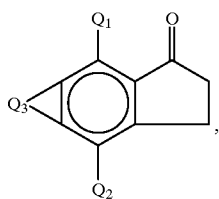

is produced in the presence of a Lewis acid by reacting the aromatic compound of the formula

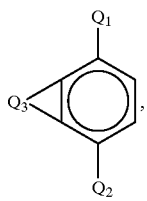

with an acrylic acid derivative of the formula

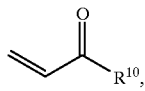

wherein
R$^{10}$ means Cl, Br, I, a hydroxyl group or a C$_1$–C$_{10}$ alkoxy group,
wherein AlCl$_3$, SbCl$_5$, FeCl$_3$, SnCl$_4$, ZnCl$_2$ or BF$_3$ is preferably suitable as the Lewis acid,
and is then further reacted in accordance with the method described in *J. Organomet. Chem.* 568 (1998), 41–51 (example 3.10) to yield an indene fused in position 5,6 of the formula

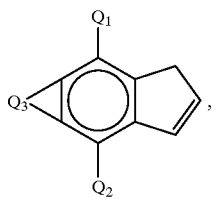

and is then further transformed into the dihalogen derivative (XIII)

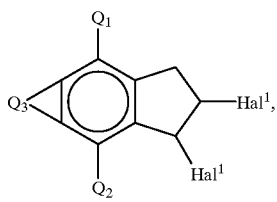

and hydrogen halide elimination is then performed. Methods for dihalogenation and subsequent hydrogen halide elimination are generally known to the person skilled in the art and are described, for example, in Patai, *The Chemistry of Halides, Pseudo-Halides and Azides*, pp. 1173–1227, New York, Wiley 1983.

Furthermore, the present invention relates to the use of the compounds of the formula (I) as catalysts both on a catalyst support (for example Al$_2$O$_3$, SiO$_2$ and other inert supports) and without a support for the polymerization of monomers from the group of C$_2$–C$_6$ α-olefins, C$_4$–C$_6$ diolefins and cyclo(di)olefins or for the copolymerization of two or more of the stated monomers, in particular for the production of amorphous, largely atactic polymers.

The present invention preferably relates to the described process and the compounds of the formula (I) producible therewith, in which Y has the meaning —Si(R$^1$R$^2$)—, —Ge(R$^1$R$^2$)— or —Si(R$^1$R$^2$)—Si(R$^3$R$^4$)—, particularly preferably —Si(R$^1$R$^2$)—, and the reaction of (II) with (i) Mg or Zn and (ii) with (III) to yield the reaction product (IV) proceeds simultaneously.

Cyclic π-systems within the meaning of Z are, for example, substituted or unsubstituted cyclopentadiene, substituted or unsubstituted 1-indene, substituted or unsubstituted 2-indene, substituted or unsubstituted fluorene, which are attached covalently to the bridge Y and ionically, covalently or coordinatively to M$^1$.

The present invention preferably relates to the process according to the present invention and to the transition metal organometallic compounds according to the present invention of the formula (I), in which, however, Z is replaced by the second ligand Z', which has the meaning of substituted or unsubstituted cyclopentadiene, substituted or unsubstituted 1-indene, substituted or unsubstituted 2-indene, substituted or unsubstituted fluorene, —N(R$^5$)—, —P(R$^6$)—, |N(R$^5$R$^7$)—, |P(R$^6$R$^8$)—, —O—, —S—, |OR$^5$— or |SR$^5$—, in which R$^5$ to R$^8$ and the vertical lines have the above-stated meaning.

Further preferred second ligands are those of the formula Z" with the range of meaning of —N(R$^5$)— or |N(R$^5$R$^7$)—, in particular in conjunction with Y=—Si(R$^1$R$^2$)— and M$^1$=Ti or Zr.

Compounds of the formula (I), in which Y=—Si(R$^1$R$^2$)—, M$^1$=Ti or Zr and Z=—N(R$^5$)— are suitable in particular for the production of atactic polypropylene.

Linear or branched C$_1$–C$_{10}$ alkyl is, for example, methyl, ethyl, propyl, isopropyl, butyl, isobutyl, tert.-butyl, the isomeric pentyls, hexyls, octyls or decyls. C$_1$–C$_4$ alkyl is preferred, with methyl and ethyl being particularly preferred.

C$_5$–C$_8$ cycloalkyl is, for example, cyclopentyl, methylcyclopentyl, dimethylcyclopentyl, cyclohexyl, methylcyclohexyl, dimethylcyclohexyl, cycloheptyl, cyclooctyl, preferably cyclopentyl and cyclohexyl and the methyl and dimethyl derivatives thereof.

C$_6$–C$_{14}$ aryl is, for example, phenyl, naphthyl, biphenylyl, anthryl, phenanthryl, preferably phenyl.

C$_7$–C$_{10}$ aralkyl is, for example, benzyl, α- or β-phenylethyl, phenylpropyl or phenylbutyl.

C$_1$–C$_4$ alkoxy or C$_1$–C$_4$ alkylthio are, for example, methoxy, methylthio, ethoxy, ethylthio, propoxy, propylthio, isopropoxy, isopropylthio, butoxy, butylthio, isobutoxy and isobutylthio.

Aryl or the aromatic moieties of aralkyl may be identically or differently mono- or disubstituted by fluorine, chlorine, bromine, methyl, ethyl, methoxy or ethoxy.

Q$^3$ is for example —(CR$^{11}$$_2$)$_m$—, where m=2, 3, 4, 5 or 6, wherein R$^{11}$ has the range of meaning of R$^1$ to R$^4$, more preferably —(CH$_2$)$_m$—, where m=3, 4.

Halogen within $R^1$ to $R^8$ is, for example, fluorine, chlorine, bromine or various thereof, preferably chlorine.

$M^1$ is for example Ti, Zr, Hf, V, Nb, Ta, Cr, W, Mo, preferably Ti, Zr, Hf, V, Nb, more preferably Ti, Zr, Hf, and most preferably Ti, Zr. $M^1$ may be used both in the highest possible oxidation state and in a different, lower oxidation state and may occur in this form in the organometallic compounds. In many cases, it is advantageous initially to use $M^1$ in a lower oxidation state and then to oxidize it to a higher valency with a mild oxidizing agent, for example $PbCl_2$.

X is a singly or multiply charged anion from the group of fluoride, chloride, bromide, $C_1$–$C_4$ carboxylate, amide, $C_1$–$C_4$ alkyl, phenyl, benzyl, neopentyl and substituted or unsubstituted butadienyl, preferably chloride or fluoride; various of the stated anions may also be present.

$Hal^1$, $Hal^2$ and $Hal^3$ within (II) and (III) are mutually independently Cl, Br or I, with $Hal^1$ preferably being Br and $Hal^2$ and $Hal^3$ being Cl or Br.

The temperature for the reaction of (II) with Mg or Zn is in the range from –20° C. to +120° C., preferably from 0° C. to +100° C., more preferably +25° C. to +80° C.

The quantity of Mg or Zn is 1 to 100 mol per mol of (II). Quantities outside the stated range may, in principle, also be used. Below 1 mol of Mg or Zn per mol of (II), the reaction of (II) is incomplete and above 100 mol, no further advantage may be anticipated with regard to the completeness and rate of the reaction. Preferably, 1 to 10 mol of Mg or Zn, more preferably 1 to 5 mol of Mg or Zn, are used per mol of (II). Of the metals Mg and Zn, Mg is preferred for the reaction.

The temperature for the further reaction with (III) is likewise in the range from –20° C. to +120° C., preferably from 0° C. to +100° C., and most preferably from +25° C. to +80° C.

The quantity of (III) is 1 to 20 mol per mol of (II). The above statement with regard to the quantity of Mg or Zn applies to quantities outside this range. Preferably, 1 to 10 mol of (III), more preferably 1 to 2 mol of (III), are used per mol of (II).

Unreacted Mg or Zn and (III) are separated from the reaction batch in a manner known to the person skilled in the art and may be reused.

The process according to the present invention may be performed in the presence of a polar, aprotic solvent. Suitable solvents are for example, methylene chloride, chloroform, dimethylformamide, N-methylpyrrolidone and ethers. Of these, the ethers are preferred, for example, diethyl ether, diisopropyl ether, dioxane, tetrahydrofuran and others known to the person skilled in the art. The quantity of solvent is selected such that (II) and the organomagnesium or organozinc compound arising therefrom are in dissolved form and the unreacted Mg or Zn may be separated, for example, by filtration or decanting or an analogous separation operation. This quantity is, for example, 50 to 1000% of the quantity of (II).

Y is preferably —$C(R^1R^2)$—, —$Si(R^1R^2)$—, particularly preferably —$Si(R^1R^2)$—.

In the event that Y has the meaning —$Si(R^1R^2)$—, —$Ge(R^1R^2)$— or —$Si(R^1R^2)$—$Si(R^1RK)$—, simultaneously reacting (II) with (i) Mg or Zn and (ii) with (III) is an elegant way of saving one reaction step.

In the event that the reaction of (IV) with (Va) or (Vb) to yield (VII) is performed in the presence of an auxiliary base, the following may be considered for this purpose: open-chain or cyclic tertiary aliphatic amines having a total of 3 to 30 C atoms, such as trimethylamine, triethylamine, tripropylamine, triisopropylamine, tributylamine, triisobutylamine, trihexylamine, trioctylamine, tridecylamine, N-methylpiperidine, N,N'-dimethylpiperazine, diazabicyclononane (DBN), diazabicycloundecane (DBU), as well as amines with differing C chain lengths, such as N,N-dimethylbutylamine, N,N-dimethyloctylamine, N,N-dimethylstearylamine and the like, and aromatic amines, such as pyridine, methylpyridine, quinoline, N,N-dimethylaniline and the like.

The reaction mixture containing the organometallic compound (I) is worked up using operations known to the person skilled in the art, such as filtration, removal of volatile mixture constituents by distillation and crystallization.

The organometallic compounds of the formula (I) may be used as catalysts for (co)polymerizing $C_2$–$C_{12}$ α-olefins, $C_4$–$C_{20}$ diolefins, cyclo(di)olefins or mixtures of two or more thereof. Monomers from the stated groups are, for example: ethylene, propylene, 1-butylene, 1-pentene, 1-hexene, 1-octene and the branched isomers thereof, isobutylene, 1,3-butadiene, 1,3- or 1,4-pentadiene, 1,3-, 1,4- or 1,5-hexadiene, 1,5-heptadiene, isoprene, chloroprene, norbornene, 5-ethylidene-2-norbornene, 5-vinyl-2-norbornene, 4-vinyl-1-cyclohexene, dicyclopenta-diene, 7-methyl-1,6-octadiene and 5,7-dimethyl-1,6-octadiene.

The compounds of the formula (I) are frequently used for (co)polymerization in combination with co-catalysts.

Co-catalysts which may be considered are co-catalysts known in the field of metallocenes, such as polymeric or oligomeric alumoxanes, Lewis acids as well as aluminates and borates. In this connection, reference is in particular made to *Macromol. Symp.* vol. 97, July 1995, pp. 1–246 (for alumoxanes), and to EP-A1-277 003, EP-A1-277 004, *Organometallics* 1997, 16, 842–857 (for borates) and EP-A2-573 403 (for aluminates).

Suitable co-catalysts are, in particular, methylalumoxane, methylalumoxane modified by triisobutylaluminum (TIBA), as well as diisobutylalumoxane, trialkylaluminum compounds, such as trimethylaluminum, triethylaluminum, triisobutylaluminum, triisooctyl-aluminum, furthermore dialkylaluminum compounds such as diisobutylaluminum hydride, diethylaluminum chloride, substituted triarylboron compounds, such as tris(pentafluorophenyl)borane, as well as ionic compounds containing tetrakis(pentafluorophenyl) borate as the anion, such as triphenylmethyl tetrakis (pentafluorophenyl)borate, trimethyl-ammonium tetrakis (pentafluorophenyl)borate, N,N-dimethylanilinium tetrakis (pentafluorophenyl)borate, substituted triarylaluminum compounds, such as tris(pentafluorophenyl)aluminum, as well as ionic compounds containing tetrakis (pentafluorophenyl)aluminate as the anion, such as triphenylmethyl tetrakis(pentafluorophenyl)-aluminate, N,N-dimethyl-anilinium tetrakis(pentafluorophenyl)aluminate.

It is, of course, possible to use the co-catalysts as a mixture with each other. The most favorable mixing ratios should be determined by suitable preliminary testing. Such (co)polymerization reactions are performed in the gas, liquid or slurry phase. The temperature range for this purpose extends from –20° C. to +200° C., preferably from 0° C. to 160° C., more preferably from +20° C. to +80° C.; the pressure range extends from 1 to 50 bar, preferably from 3 to 30 bar. Additionally used solvents are, for example: saturated aliphatics or (halo)aromatics, such as pentane, hexane, heptane, cyclohexane, petroleum ether, kerosene, hydrogenated naphthas, benzene, toluene, xylene, ethylbenzene, chlorobenzene and the like. These reaction conditions for (co)polymerization are known in principle to the person skilled in the art.

Important polymers which may be produced with the organometallic compounds according to the present invention as catalysts, are those of ethylene and the copolymers thereof. Suitable comonomers are $C_2$–$C_{12}$ alkenes, such as ethylene, 1-butene, 1-pentene, 1-hexene, 1-octene and arylalkenes, such as for example styrene. Further suitable comonomers are unconjugated dienes, such as 1,4-hexadiene, 1,5-heptadiene, 4-vinyl-1-cyclohexene, 7-methyl-1,6-octadiene and 5,7-dimethyl-1,6-octadiene, 5-ethylidene-2-norbornene, 5-vinyl-2-norbornene and dicyclopentadiene. It is possible also to use mixtures of the stated comonomers.

The ethylene (co)polymers producible in this manner have molecular weights with $M_w$=>100000 g/mol and molecular weight distributions with $M_w/M_n$=<4. The ethylene (co)polymers have intrinsic viscosities of greater than 1 dl/g, preferably of greater than 2 dl/g. Crystallinity values are less than 15%, wherein percentage crystallinity=(melt enthalpy/209 J/g)×100 and melt enthalpy is determined in J/g using the DSC method. Ethylene (co)polymers having melt enthalpies with a value of less than 5 J/g (DSC method) are more preferred. The ethylene (co)polymers are readily soluble in usual solvents such as hexane, heptane, diethyl ether or toluene.

It is in particular possible also to produce rubbers based on ethylene and one or more of the stated comonomers in the described manner. It is more preferred to copolymerize ethylene and propylene, wherein amorphous ethylene (co) polymers having an ethylene content in the polymer in the range from 30 to 70 wt. %, preferably from 40 to 65 wt. %, are obtained.

EPDM rubbers based on ethylene, propylene and a diene, preferably 5-ethylidene-2-norbornene, may also be produced in the described manner. The EPDM rubbers are distinguished in that they have elevated molecular weights and low crystalline contents.

High molecular weight atactic polymers, for example atactic polypropylene, may particularly effectively be produced using the organometallic compounds according to the present invention.

For example, the (co)polymerization of ethylene with or without the stated comonomers may be performed as follows: after conventional cleaning operations, a steel autoclave is charged with a solvent and a scavenger, for example triisobutylaluminum. The scavenger renders harmless any possible contaminants and catalyst poisons, for example water or other compounds containing oxygen. A compound of the formula (I) is then added as a catalyst precursor. The reactor is then charged with monomers up to a certain pressure, adjusted to a selected temperature and the polymerization initiated by adding one or more of the above-stated co-catalysts. Polymerization may proceed in a continuous or discontinuous process.

The invention is further illustrated but is not intended to be limited by the following examples in which all parts and percentages are by weight unless otherwise specified.

EXAMPLES

The following Examples illustrate the invention in greater detail.

General information: The organometallic compounds were prepared and handled with exclusion of air and moisture under a protective argon atmosphere (Schlenk technique). All the solvents required were converted into absolute form before use by several hours' boiling over a suitable desiccant and subsequent distillation under argon. The compounds were characterized by $^1$H-NMR, $^{13}$C-NMR and infrared spectroscopy.

Polymer Characterization

Intrinsic viscosity was determined in an Ubbelohde capillary viscosimeter at 140° C. in o-dichlorobenzene as solvent (multipoint measurement). DSC measurements were made in a Perkin-Elmer DSC-2 Differential Scanning Calorimeter using the following method: two heating phases −90° C. to +180° C., heating rate 20 K/min, rapid cooling at 320 K/min to −90° C., nitrogen flushing, initial sample weights 12.3 mg in standard capsules. NMR measurements to determine microstructure were performed in tetrachloroethane using a Bruker DRX-400 instrument. Mooney viscosity was determined in accordance with ASTM 1646/DIN 53 523. Polymer composition was determined by IR spectroscopy in accordance with ASTM D 3900.

| Abbreviations | |
|---|---|
| of th. | of theoretical |
| rel. to | relative to |
| TIBA | triisobutylaluminum |
| I.V. | intrinsic viscosity |
| Tg | glass transition temperature |

Example 1

Preparation of 5,6,7-tetrahydroindacen-1-one

Indan (60.0 g, 62.6 ml, 0.5 mol) and acryloyl chloride (45.9 g, 41.0 ml, 0.5 mol) were dissolved in 600 ml of anhydrous methylene chloride in a 1 l three-necked flask with reflux condenser. The temperature was reduced to 0° C. and aluminum trichloride (135.0 g, 1.0 mol) was added slowly in portions. The temperature was raised to 25° C. within 30 minutes and stirring was continued for a further 15 h. The reaction mixture was then refluxed for 1 h. After cooling, the reaction mixture was poured onto approx. 1000 g of ice in a 2 l beaker. After standing for 15 h, the organic phase was separated and the aqueous phase washed once with 100 ml of $CH_2Cl_2$. The combined organic phases were dried with anhydrous $Na_2SO_4$ and the volatile constituents removed in a rotary evaporator. The resultant brown oil was initially purified by filtration through silica gel with methylene chloride (in two portions, column dimensions: 4×20 cm, methylene chloride, 25° C.). After removal of the solvent, the brown crude product was distilled in a microdistillation apparatus without cooling under an oil pump vacuum. A light yellow solid was obtained which distilled over at 115 to 125° C. at 2 mbar (oil bath: 170 to 190° C.).

| | |
|---|---|
| Yield | 21.0 g of 5,6,7-tetrahydroindacen-1-one (0.12 mol, 24% of th., rel to introduced indan) |
| IR (KBr) [cm$^{-1}$] | 3039 (s); 2953 (s); 2918 (s), 2841 (s); $v_{co}$ = 1692 (bs); 1611 (s); 1573 (s); 1435 (s); 1304 (s); 1247 (s). |
| $^1$H NMR (CDCl$_3$) | δ 7.54 (s,1H,C$_{arom.}$—H); 7.27 (s,1H,C$_{arom.}$—H); 3.05 (t,2H,$^3$J$_{HH}$=6.0 Hz, CO—CH$_2$), 2.93 (t,2H,$^3$J$_{HH}$=8.0 Hz, CH$_2$—CH$_2$—CH=), 2.90 (t,2H,$^3$J$_{HH}$=8.0 Hz, CH$_2$—CH$_2$—CH=), 2.66 (t,2H,$^3$J$_{HH}$=6.0 Hz, CO—CH$_2$—CH$_2$), 2.10 (pq,2H,$^3$J$_{HH}$=8.0 Hz, CH$_2$—CH$_2$—CH=). |
| $^{13}$C NMR (CDCl$_3$) | δ 206.5 (C=O), 154.3 (C—CH$_2$—CH$_2$), 152.8 (C—CH$_2$—CH$_2$), 144.0 (C—CH$_2$—CO), 135.0 (C—CH$_2$—CH$_2$—CO), 122.0 (CH,C$_{arom.}$), 118.8 (CH,C$_{arom.}$), 36.7 (CH$_2$), 33.0 (CH$_2$), 31.9 (CH$_2$), 25.8 (CH$_2$), 25.5 (CH$_2$). |

Example 2

Preparation of 5,6,7-tetrahydroindacen-1-ol 5,6,7-Tetrahydroindacen-1-one (20.0 g, 0.125 mol) was dissolved in 100 ml of absolute diethyl ether. Finely divided NaBH$_4$ (4.06 g, 0.125 mol) was added at 0° C. 50 ml of absolute ethanol was then slowly added dropwise. After stirring for 15 h at 25° C. (caution, evolution of H$_2$!), the suspension was poured onto ice. A colorless solid was formed. After acidification with 150 ml of 1 M HCl and addition of a further 50 ml of diethyl ether, the organic phase was washed twice with 25 ml portions of 1 molar HCl and the phase containing HCl was separated. After removal of all volatile constituents in a rotary evaporator, a colorless solid, 5,6,7-tetrahydroindacen-1-ol, was obtained, which was used without further purification in Example 3.

Example 3

Preparation of 5,6,7-tetrahydroindacene

To this end, the 5,6,7-tetrahydroindacen-1-ol prepared in Example 2 was dissolved in 200 ml of benzene and combined with 300 mg of p-toluenesulfonic acid. The mixture was refluxed with a water separator (4 to 5 h), so removing the water formed during the reaction. The reaction solution was then washed twice with 25 ml portions of 1 molar NaHCO$_3$, then the benzene was removed in a rotary evaporator. The resultant residue was purified by column chromatography (column dimensions: 4×20 cm, silica gel, petroleum ether, 25° C.). A colorless oil was obtained at 25° C., which solidified in the refrigerator.

| Yield | 16.3 g of 5,6,7-tetrahydroindacen (0.113 mol, 90% of th., rel. to introduced ketone) |
|---|---|
| IR (NaCl) [cm$^{-1}$] | 3059 (m), 2997 (m), 2952 (m), 2881 (m), 2838 (m), 1853 (m), 1732 (wide, m), 1616 (s), 1543 (s), 1455 (wide, s), 938 (wide, s), 861 (wide, s), 813 (wide, s). |
| $^1$H NMR (CDCl$_3$) | δ 7.41 (s,1H,C$_{arom.}$—H), 7.38 (s,1H,C$_{arom.}$—H), 6.92 (d,1H,$^3$J$_{HH}$=5.0 Hz, C—C$\underline{H}$—CH—CH$_2$), 6.57 (d,1H,$^3$J$_{HH}$=5.0 Hz, C—CH=C$\underline{H}$—CH$_2$), 3.43 (s,2H,C—CH=CH—C$\underline{H}_2$), 3.00 (pt,4H,$^3$J$_{HH}$=7.5 Hz, CH$_2$—C$\underline{H}_2$—CH=), 2.19 (pq,2H,$^3$J$_{HH}$=7.5 Hz, C$\underline{H}_2$—CH$_2$—CH=). |
| $^{13}$C NMR (CDCl$_3$) | δ 143.3 (C$_{arom.}$), 142.2 (C$_{arom.}$), 142.1 (C$_{arom.}$), 140.8 (C$_{arom.}$), 133.3 (C—C$\underline{H}$=CH—CH$_2$), 131.9 (C—CH=C$\underline{H}$—CH$_2$), 119.8 (C$_{arom.}$—H), 116.8 (C$_{arom.}$—H), 38.5 (CH$_2$), 32.65 (CH$_2$), 32.60 (CH$_2$), 25.9 (CH$_2$). |

Example 4

Preparation of 1,2-dibromo-5,6,7-tetrahydroindacane 5,6,7-Tetrahydroindacene (7.6 g, 0.0486 mol) from Example 3 was dissolved in 100 ml of diethyl ether. Bromine (7.8 g, 2.5 ml, 0.0486 mol) was slowly added dropwise at 0° C. The mixture was stirred for 1 h at 0° C. and then for 12 h at 25° C. The diethyl ether was removed in a rotary evaporator and the residue chromatographed through silica gel (column dimensions: 4×20 cm, methylene chloride/hexane=1:10, 25° C.). 1,2-Dibromo-5,6,7-tetrahydroindacane was obtained as a light yellow oil.

| Yield | 11.8 g of 1,2-dibromo-5,6,7-tetrahydroindacane (0.0373 mol, 77% of th., rel. to introduced 5,6,7-tetrahydroindacene). |
|---|---|
| IR (NaCl) [cm$^{-1}$] | 3011 (s), 2947 (wide, s), 2893 (s), 2851 (s), 1746 (w), 1618 (w), 1436 (wide, s), 1315 (s), 1284 (s), 1254 (s), 1208 (s), 1145 (s), 945 (w), 915 (m). |
| $^1$H NMR (CDCl$_3$) | δ 7.51 (s,1H,C$_{arom.}$—H), 7.25 (s,1H,C$_{arom.}$—H), 6.51 (s,1H, C$_{arom.}$—C$\underline{H}$Br—CHBr)$^1$, 4.74 (d,1H,$^3$J$_{HH}$=4.0 Hz, C$_{arom.}$—CHBr—C$\underline{H}$Br), 3.62 (dd,1H,$^3$J$_{HH}$=4.0, 12.0 Hz, C$_{arom.}$—C$\underline{H}_2$—CHBr), 3.05 (d,1H,$^3$J$_{HH}$=12.0 Hz, C$_{arom.}$—C$\underline{H}_2$—CHBr). |
| $^{13}$C NMR (CDCl$_3$) | δ 147.2 (C$_{arom.}$), 144.9 (C$_{arom.}$), 139.4 (C$_{arom.}$), 138.9 (C$_{arom.}$), 122.0 (C$_{arom.}$), 121.8 (C$_{arom.}$), 59.2 (CHBr), 55.5 (CHBr), 41.6 (CH$_2$), 33.5 (CH$_2$), 33.3 (CH$_2$), 26.2 (CH$_2$). |

Example 5

Production of 2-bromo-2,5,7-tetrahydroindacene 1,2-Dibromo-5,6,7-tetrahydroindacane (11.9 g, 0.0373 mol) from Example 4 was dissolved in 50 ml of Tetralin and refluxed for 4 h to eliminate hydrogen bromide. The Tetralin was then removed by distillation under an oil pump vacuum. To ensure complete removal of the Tetralin, the mixture was heated to 100° C. under an oil pump vacuum for 10 minutes.

The residue was further purified by being chromatographed through silica gel. The eluent used was a mixture of methylene chloride and hexane in a 1:3 ratio. The resultant crude product was purified by crystallisation from methanol. Colorless crystals of 2-bromo-5,6,7-tetrahydroindacene were obtained.

| Yield | 1.2 g of 2-bromo-5,6,7-tetrahydroindecene (0.0051 mol, 14% of th., rel. to introduced 1,2-dibrom-5,6,7-tetrahydroindacane). |
|---|---|
| Melting point | 95° C. |
| IR (KBr) [cm$^{-1}$] | 3013 (w), 2944 (s), 2842 (s), 1544 (m), 1459 (s), 1391 (s), 1255 (s), 877 (s). |
| $^1$H NMR (CDCl$_3$) | δ 7.24 (s,1H,C$_{arom.}$—H), 7.18 (s,1H,C$_{arom.}$—H), 6.78 (s,1H,C$_{arom.}$—C$\underline{H}$=CBr), 3.55 (s,2H,CH=CBr—C$\underline{H}_2$), 2.93 (pt,4H,$^3$J$_{HH}$=7.5 Hz, CH$_2$—C$\underline{H}_2$—CH=), 2.12 (pq,4H,$^3$J$_{HH}$=7.5 Hz, C$\underline{H}_2$—CH$_2$—CH=). |
| $^{13}$C NMR (CDCl$_3$) | δ 143.0 (C$_{arom.}$), 142.7 (C$_{arom.}$), 141.5 (C$_{arom.}$), 141.3 (C$_{arom.}$), 133.6 (C$\underline{H}$=CBr), 123.8 (CBr), 119.9 (C$_{arom.}$—H), 116.6 (C$_{arom.}$—H), 45.4 (CBr—C$\underline{H}_2$), 33.1 (C$\underline{H}_2$—CH$_2$—C$_{arom.}$), 33.1 (C$\underline{H}_2$—CH$_2$—C$_{arom.}$), 26.1 (CH$_2$—C$\underline{H}_2$—C$_{arom.}$). |

Example 6

Preparation of [5,6,7-tetrahydroindacenyl] dimethylchlorosilane

2-Bromo-5,6,7-tetrahydroindacene (1.2 g, 0.0051 mol) from Example 5 was dissolved in 4.0 ml of tetrahydrofuran and slowly added to a mixture consisting of magnesium (0.2 g, 0.008 mol), dichlorodimethyl-silane (1.5 g, 1.3 ml, 0.012 mol) in 2 ml of tetrahydrofuran. The temperature of the reaction mixture rose to 60° C. during this addition. After stirring at 25° C. for 15 h, all the volatile constituents are removed under an oil pump vacuum and the residue redissolved in 50 ml of petroleum ether.

The precipitated magnesium salts were removed by filtration (flitted filter) and the solvent removed from the filtrate under an oil pump vacuum. A light yellow, waxy solid was obtained, which was used without further purification for synthesizing $^t$butylamine-2-[5,6,7-tetrahydroindacenyl]-dimethylsilane (Example 7).

Yield: 1.23 g of [5,6,7-tetrahydroindacenyl] dimethylchlorosilane (4.94 mmol, 97% of th., rel. to introduced 2-bromo-5,6,7-tetrahydroindacene).

Example 7

Preparation of ᵗbutylamin-2-[5,6,7-tetrahydroindacenyl]dimethylsilane

To this end, the [5,6,7-tetrahydroindacenyl] dimethylchlorosilane obtained in Example 6 was dissolved in 20.0 ml of diethyl ether, cooled to 0° C. and combined with ᵗbutylamine (2.0 ml, 0.025 mol) in a single portion. The mixture was stirred for 15 hours at 25° C. All the volatile constituents were then removed. The residue was redissolved in 40 ml of petroleum ether and the precipitated ammonium salt separated by filtration. All the volatile constituents were removed from the filtrate under an oil pump vacuum. A light yellow oil of ᵗbutylamine-2-[5,6,7-tetrahydroindacenyl]dimethylsilane was obtained.

| | |
|---|---|
| Yield | 1.32 g of ᵗbutylamine-2-[5,6,7-tetrahydroindacenyl]dimethylsilane (4.6 mmol, 94% of th., rel. to introduced 2-bromo-5,6,7-tetrahydroindacene). |
| IR (NaCl) [cm$^{-1}$] | 3382 (m), 3053 (w), 3004 (m), 2959 (s), 2893 (s), 2844 (m), 1533 (m), 1462 (m), 1376 (m), 1251 (s), 1225 (s), 1090 (wide, m), 1035 (wide, m), 849 (wide, s). |
| $^1$H NMR (CDCl$_3$) | δ 7.22 (s,1H,C$_{arom.}$—H), 7.14 (s,1H,C$_{arom.}$—H), 7.01 (s,1H,C$_{arom.}$—C$\underline{H}$=CSi), 3.42 (s,2H,CH=CSi—C$\underline{H}_2$), 2.93 (pt,4H,$^3$J$_{HH}$=7.0 Hz, CH$_2$—C$\underline{H}_2$—CH=), 2.01 (pq,4H,$^3$J$_{HH}$=7.0 Hz, C$\underline{H}_2$—CH$_2$—CH=), 1.05 (s,9H,C(CH$_3$)$_3$), 0.20 (s,6H,Si(CH$_3$)$_2$). |
| $^{13}$C NMR (CDCl$_3$) | δ 148.6 (C$_{arom.}$—Si), 144.3 (C$_{arom.}$), 143.3 (C$_{arom.}$), 141.1 (C$_{arom.}$), 140.0 (C$_{arom.}$), 139.7 (C$\underline{H}$=CSi), 118.5 (C$_{arom.}$—H), 115.4 (C$_{arom.}$—H), 48.3 ($\underline{C}$(CH$_3$)$_3$), 40.5 (CH=CSiC$\underline{H}_2$), 32.6 (C($\underline{C}$H$_3$)$_3$), 31.5 (CH$_2$—$\underline{C}$H$_2$—C$_{arom.}$), 31.4 (CH$_2$—$\underline{C}$H$_2$—C$_{arom.}$), 24.9 ($\underline{C}$H$_2$—CH$_2$C$_{arom.}$), 0.0 (Si($\underline{C}$H$_3$)$_2$). |

Example 8

Preparation of ᵗbutylamine-2-[5,6,7-tetrahydroindacenyl]-dimethylsilyltitanium dichloride ᵗButylamine-2-[5,6,7-tetrahydroindacenyl]dimethylsilane (0.61 g, 0.00213 mol) from Example 7 was dissolved in 15 ml of n-pentane and combined dropwise at −78° C. with 1.7 ml of a 2.5 M solution of n-BuLi in hexane. The mixture was stirred for 1 h at −78° C. and then for a further 2 h at 25° C. The solvent was removed under an oil pump vacuum, the remaining light orange powder was dissolved at −78° C. in 20 ml of tetrahydrofuran and transferred by means of a cannula at −78° C. into a suspension of TiCl$_3$.3THF in 10 ml of tetrahydrofuran, wherein the color changed to deep yellow. After stirring for 1 h at −78° C. and 1 h at 25° C., solid, finely divided lead dichloride (0.592 g, 0.00213 mol) was added and the mixture stirred for 0.5 h at 25° C. The suspension then turned red-brown. The solvent was removed and the residue extracted twice with 10 ml portions of toluene. The insoluble constituents of the suspension were allowed to settle and the supernatant solution was transferred by means of a cannula into a Schlenk flask. The toluene was removed and the residue redissolved in 2 ml of petroleum ether. A red-brown solid was deposited at 25° C.

| | |
|---|---|
| Yield | 0.5 g of ᵗbutylamine-2-[5,6,7-tetrahydroindacenyl]dimethyl-silyl-titanium dichloride (1.2 mmol, 60 of th., rel. to introduced ᵗbutylamine-2-[5,6,7-tetrahydroindacenyl]dimethylsilane. |
| Melting point | 153° C. |
| IR (KBr) [cm$^{-1}$] | 2957 (s), 2875 (s), 2795 (s), 2691 (m), 2588 (m), 2493 (m), 1606 (m), 1511 (m), 1459 (m), 1433 (m), 1401 (m), 1376 (m), 1300 (w), 1250 (s), 1085 (s), 926 (wide, s), 836 (wide, s), 764 (wide, s). |
| $^1$H NMR (CDCl$_3$) | δ 7.40 (s,2H,C$_{arom.}$—H), 6.54 (s,2H,C$_{arom.}$—C$\underline{H}$=CSi), 2.92 (pt,4H,$^3$J$_{HH}$=7.0 Hz, CH$_2$—C$\underline{H}_2$—CH=), 2.03 (pq,2H,$^3$J$_{HH}$=7.0 Hz, C$\underline{H}_2$—CH$_2$—CH=), 1.30 (s,9H,C(CH$_3$)$_3$), 0.67 (s,6H,Si(CH$_{32}$). |
| $^{13}$C NMR (CDCl$_3$) | δ 147.3 (C$_{arom.}$), 134.9 (C$_{arom.}$), 119.2 (C$_{arom.}$—H), 117.9 (C$_{arom.}$—H), 113.6 (C$_{arom.}$—Si), 64.6 ($\underline{C}$(CH$_3$)$_3$), 32.5 (C($\underline{C}$H$_3$)$_3$). 32.3 (CH$_2$—$\underline{C}$H$_2$—C$_{arom.}$), 25.9 ($\underline{C}$H$_2$—CH$_2$—C$_{arom.}$), 0.0 (Si($\underline{C}$H$_3$)$_2$). |

Example 9

Polymerization of Propylene 100 ml of toluene, 0.25 ml of TIBA and 4.0 mg (10 μmol) of ᵗbutylamine-2-[5,6,7-tetrahydroindacenyl] dimethylsilyltitanium dichloride from Example 8 were initially introduced at 20° C. into a 250 ml glass reactor. Propylene was then continuously introduced into the solution with a gas inlet line at a pressure of 1.1 bar. Polymerization was initiated by adding a solution of 18.4 mg (20 pmol) of triphenylmethyl tetrakis(penta-fluorophenyl)borate in 4 ml of toluene. The temperature rose to 32° C. during polymerization. After 1 hour's polymerization, a clear highly viscous reaction solution was obtained. The reaction solution was worked up by stirring it into methanol, washing the precipitated elastic polymer with methanol and drying it in a vacuum drying cabinet. 13.8 g of amorphous, high molecular weight polypropylene were obtained. Measurement of the intrinsic viscosity revealed an I.V.=1.3 dl/g. According to DSC measurements, melt enthalpy was zero J/g. $^{13}$C-NMR spectroscopic analysis revealed the following composition: % mm=15.6 (isotactic fraction); % (mr/rm)=51.8 (atactic fraction); % mm=32.6 (syndiotactic fraction).

Example 10

Terpolymerization of ethylene, propylene and 5-ethylidene-2-norbornene (ENB)

500 ml of hexane and 1 ml of TIBA were initially introduced into a 1.4 l steel autoclave which was equipped with a mechanical stirrer, manometer, temperature sensor, temperature controller, catalyst lock and monomer metering devices for ethylene and propylene. To this mixture was added a solution of 2.0 mg (5 μmol) of ᵗbutylamin-2-[5,6,7-tetrahydroindacenyl]dimethylsilyltitanium dichloride from Example 8 in 5 ml of toluene. The internal temperature was adjusted to 40° C. with a thermostat. 16 g of ethylene and 16 g of propylene were then apportioned. Polymerization was initiated by adding a solution of 9.22 mg (10 ptmol) of triphenylmethyl tetrakis(pentafluorophenyl)borate in 5 ml of toluene. 5 ml of ENB were then added via a pressure lock. Ethylene and propylene were continuously apportioned in mass ratio of 50:50, such that the pressure was a constant 6 bar at 40° C. After 20 minutes' polymerization, another solution of 9.22 mg (10 μmol) of triphenylmethyl tetrakis (penta-fluorophenyl)borate in 5 ml of toluene was apportioned into the autoclave. After a total period of polymerization of 60 minutes, the autoclave was depressurized. The polymer was worked up by being precipitated in methanol and dried for 20 h at 60° C. under a vacuum, wherein 41.0 g of copolymer were obtained. IR spectroscopic analysis of the composition of the copolymer revealed incorporation of 47.3 wt. % of ethylene, 45.5 wt. % of propylene and 7.7 wt. % of ENB. On the basis of DSC measurement, the copolymer is completely amorphous. Melt enthalpy was zero J/g. A Tg of −48° C. was determined by the DSC method. Determination of intrinsic viscosity revealed an I.V.=4.1 dl/g.

Example 11

Terpolymerization of ethylene, propylene and 5-ethylidene-2-norbornene (ENB)

The polymerization from Example 10 was repeated, with the difference that 12 g of propylene and 18 g of ethylene were initially introduced into the autoclave, and ethylene and propylene were continually apportioned in a mass ratio of 60:40. The duration of polymerization was 60 minutes. 45.1 g of a terpolymer were obtained containing 56.9 wt. % of ethylene, 36.8 wt. % of propylene and 6.7 wt. % of ENB (IR spectroscopy). A Tg of −47° C. was determined by the DSC method. Measurement of intrinsic viscosity revealed a value of I.V.=3.1 dl/g.

Example 12

Terpolymerization of ethylene, propylene and 5-ethylidene-2-norbornene (ENB)

The polymerization from Example 10 was repeated, with the difference that 8 g of propylene and 19 g of ethylene were initially introduced into the autoclave, and ethylene and propylene were continually apportioned in a mass ratio of 70:30. The duration of polymerization was 60 minutes. 44.4 g of a terpolymer were obtained containing 64.9 wt. % of ethylene, 27.8 wt. % of propylene and 7.9 wt. % of ENB (IR spectroscopy). A Tg of −38° C. was determined by the DSC method. Measurement of intrinsic viscosity revealed a value of I.V.=3.4 dl/g.

Although the invention has been described in detail in the foregoing for the purpose of illustration, it is to be understood that such detail is solely for that purpose and that variations can be made therein by those skilled in the srt without departing from the spirit and scope of the invention except as it may be limited by the claims.

What is claimed is:

1. A process for the production of transition metal organometallic compounds with 2-indenyl fused in position 5,6 as the first ligand of the formula

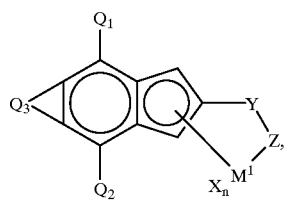

(I)

in which $Q^1$, $Q^2$ are identical or different and, as a substituent of the 2-indenyl system fused in position 5,6, mean hydrogen, $C_1$–$C_4$ alkyl, $C_6$–$C_{14}$ aryl, $C_7$–$C_{10}$ aralkyl, $C_1$–$C_4$ alkoxy, $C_1$–$C_4$ alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl, $Q^3$ represents an optionally substituted alkylene residue which, together with the two carbon atoms of the indenyl residue, forms a ring system in position 5 and 6, $M^1$ is a transition metal from groups 4, 5 or 6 of the IUPAC 1985 periodic system of elements, X means an anion, n is a number from zero to four, which is determined by the valency and bond state of $M^1$, Y represents a bridge from the group of —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— or —Si($R^1R^2$)—Si($R^3R^4$)—, in which $R^1$, $R^2$, $R^3$ and $R^4$ mutually independently mean hydrogen, halogen, linear or branched $C_1$–$C_{10}$ alkyl, $C_5$–$C_8$ cycloalkyl, $C_6$–$C_{14}$ aryl or $C_7$–$C_{10}$ aralkyl and Z is a second ligand from the group of open-chain and cyclic, optionally anionic π-systems, —N($R^5$)—, P($R^6$)—, |N($R^5R^7$)—, |P($R^6R^8$)—, —O—, —S—, |O$R^5$—— or |S$R^5$—, wherein the horizontal line to the left of the element symbol N, P, O or S represents a covalent bond between Z and $M^1$, wherein the vertical line to the left of the element symbol N, P, O or S means an electron pair and the bond between Z and $M^1$ is of a coordinative not covalent nature and in which $R^5$, $R^6$, $R^7$ and $R^8$ mutually independently have the range of meaning of $R^1$ to $R^4$ and $R^5$ and $R^7$ may additionally mean —Si($R^1R^2R^3$) and $R^6$ and $R^8$ may additionally mean —Si($R^1R^2R^3$), —O$R^1$, —S$R^1$ or —N($R^1R^2$), comprising the step of reacting a haloindene fused in position 5,6 of the formula

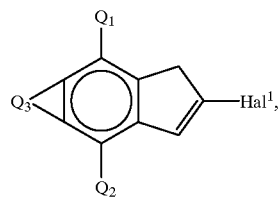

(II)

in which Hal$^1$ denotes Cl, Br or I and $Q^1$, $Q^2$ and $Q^3$ have the above meaning, with an elemental metal selected from group 1, 2 or 12 of the IUPAC 1985 periodic system or a corresponding metal compound in a quantity in the range from 1 to 100 mol of elemental metal/metal compound per mol of (II) and with a dihalide of the bridge Y of the formula Hal$^2$-Y-Hal$^3$        (III), in which Hal$^2$ and Hal$^3$ mutually independently represent Cl, Br or I and Y has the above range of meaning, in a quantity of 1 to 20 mol of (III) per mol of (II), wherein in the event that Y has the meaning —Si($R^1R^2$)—, —Ge ($R^1R^2$)— or —Si($R^1R^2$)—Si($R^3R^4$)—, the reaction of (II) with (i) metal/metal compound and (ii) with (III) may also proceed simultaneously, and the reaction product of the formula

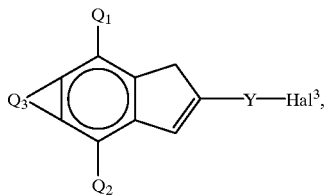

in which $Q^1$, $Q^2$, $Q^3$, Y and $Hal^3$ have the above meaning, optionally after the isolation thereof, is reacted with a Z derivative of the formula $$ZM^2_p \qquad (Va)$$

or $$ZR^9_p \qquad (Vb),$$

in which
- $M^2$ denotes Li, Na, K or —$MgHal^4$, in which $Hal^4$ has the range of meaning of $Hal^2$,
- p represents the number one or two,
- $R^9$ represents hydrogen, —$Si(R^1R^2R^3)$ or $Sn(R^1R^2R^3)$ and
- Z, $R^1$, $R^2$ and $R^3$ have the above meaning, optionally in the presence of an auxiliary base to yield the 2-indenyl compound of the formula

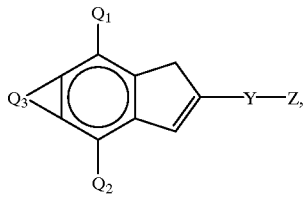

in which $Q^1$, $Q^2$, $Q^3$, Y and Z have the above meaning, and which may be present as a dianion and in which Z may furthermore bear $M^2$, $R^9$ or an electron pair, and is then further reacted with a transition metal compound of the formula $$M^1X_q \qquad (VIII),$$

in which
- $M^1$ and X have the above meaning and
- q is a number from two to six, which is determined by the oxidation state of $M^1$.

2. A process according to claim 1, wherein Y is a bridge selected from the group consisting of —$Si(R^1R^2)$—, —$Ge(R^1R^2)$— and —$Si(R^1R^2)$—$Si(R^3R^4)$—, and the reaction of (II) with (i) an elemental metal/metal compound and (ii) with (III) to yield the reaction product proceeds simultaneously.

3. A process according to claim 2, wherein Y is a bridge —$Si(R^1R^2)$—.

4. A process according to claim 1, wherein said elemental metal is Mg or Zn or a mixture of Mg and Zn.

5. A process according to claim 1, wherein $M^1$ is a transition metal selected from the group consisting of Ti, Zr, Hf, V, Nb.

6. A process according to claim 5, wherein $M^1$ is a transition metal selected from the group consisting of Ti, Zr and Hf.

7. A process according to claim 6, wherein $M^1$ is a transition metal selected from the group consisting of Ti and Zr.

8. A process according to claim 1, wherein 1 to 10 mol of elemental metal/metal compound per mol of (II) and 1 to 10 mol of (III) per mol of (II) are used.

9. Transition metal organometallic compounds with 2-indenyl fused in position 5,6 as the first ligand of the formula

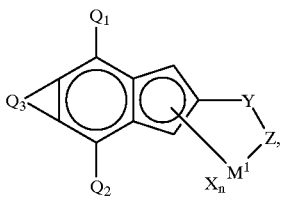

in which
- $Q^1$, $Q^2$ are identical or different and, as a substituent of the 2-indenyl system fused in position 5,6, mean hydrogen, $C_1$–$C_4$ alkyl, $C_6$–$C_{14}$ aryl, $C_7$–$C_{10}$ aralkyl, $C_1$–$C_4$ alkoxy, $C_1$–$C_4$ alkylthio, phenoxy, phenylthio, di-$C_1$–$C_4$-alkylamino, $C_6$–$C_{14}$-aryl-$C_1$–$C_4$-alkylamino, di-$C_6$–$C_{14}$-arylamino, dibenzylamino, tri-$C_1$–$C_4$-alkylsilyl, di-$C_1$–$C_4$-alkylboranyl, phenyl-$C_1$–$C_4$-alkylboranyl, diphenylboranyl, di-$C_1$–$C_4$-alkylphosphoryl, diphenylphosphoryl or phenyl-$C_1$–$C_4$-alkylphosphoryl,
- $Q^3$ represents an optionally substituted alkylene residue which, together with the two carbon atoms of the indenyl residue, forms a ring system in position 5 and 6,
- $M^1$ is a transition metal from groups 4, 5 or 6 of the IUPAC 1985 periodic system of elements,
- X means an anion,
- n is a number from zero to four, which is determined by the valency and bond state of $M^1$,
- Y represents a bridge from the group of —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— or —$Si(R^1R^2)$—$Si(R^3R^4)$—, in which $R^1$, $R^2$, $R^3$ and $R^4$ mutually independently mean hydrogen, halogen, linear or branched $C_1$–$C_{10}$ alkyl, $C_5$–$C_8$ cycloalkyl, $C_6$–$C_{14}$ aryl or $C_7$–$C_{10}$ aralkyl and
- Z is a second ligand from the group of open-chain and cyclic, optionally anionic π-systems, —$N(R^5)$—, $P(R^6)$—, $|N(R^5R^7)$—, $IP(R^6R^8)$—, —O—, —S—, $|OR^5$— or $|SR^5$—, wherein the horizontal line to the left of the element symbol N, P, O or S represents a covalent bond between Z and Ml, wherein the vertical line to the left of the element symbol N, P, O or S means an electron pair and the bond between Z and $M^1$ is of a coordinative not covalent nature and in which $R^5$, $R^6$, $R^7$ and $R^8$ mutually independently have the range of meaning of $R^1$ to $R^4$ and $R^5$ and $R^7$ may additionally mean —$Si(R^1R^2R^3)$ and $R^6$ and $R^8$ may additionally mean —$Si(R^1R^2R^3)$, —$OR^1$, —$SR^1$ or —$N(R^1R^2)$.

10. Transition metal organometallic compounds according to claim 9, in which, in the formula (I), Z is replaced by the second ligand Z', which has the meaning of substituted or unsubstituted cyclopentadienyl, substituted or unsubstituted 1-indenyl, substituted or unsubstituted 2-indenyl, substituted or unsubstituted fluorenyl, —N($R^5$)—, —P($R^6$)—, |N($R^5R^7$)—, |P($R^6R^8$)—, —O—, —S—, |O$R^5$— or |S$R^5$—.

11. Transition metal organometallic compounds according to claim 9, in which, in the formula (I), Z' is replaced by the second ligand Z", which has the meaning of —N($R^5$)— or |N($R^5R^7$)—, wherein in the formula (I) Y furthermore means —Si($R^1R^2$)— and $M^1$ means Ti or Zr.

12. A transition metal organometallic compound according to claim 9, wherein said compound is tert.-butylamine-2-[5,6,7-tetrahydroindacenyl]dimethylsilyltitanium dichloride.

* * * * *